US012758144B2

(12) United States Patent
Rogers, Jr. et al.

(10) Patent No.: US 12,758,144 B2
(45) Date of Patent: Oct. 13, 2026

(54) HEAD AND NECK FULL MOTION TESTING SYSTEM

(71) Applicant: BON SECOURS MERCY HEALTH, INC., Cincinnati, OH (US)

(72) Inventors: Burton L. Rogers, Jr., Toledo, OH (US); David Michael Uhlenhake, North Baltimore, OH (US)

(73) Assignee: BON SECOURS MERCY HEALTH, INC., Cincinnati, OH (US)

( * ) Notice: Subject to any disclaimer, the term of this patent is extended or adjusted under 35 U.S.C. 154(b) by 586 days.

(21) Appl. No.: 17/924,881

(22) PCT Filed: May 19, 2021

(86) PCT No.: PCT/US2021/033115
§ 371 (c)(1),
(2) Date: Nov. 11, 2022

(87) PCT Pub. No.: WO2021/236743
PCT Pub. Date: Nov. 25, 2021

(65) Prior Publication Data
US 2023/0181097 A1 Jun. 15, 2023

Related U.S. Application Data

(60) Provisional application No. 63/027,458, filed on May 20, 2020.

(51) Int. Cl.
*A61B 5/00* (2006.01)
*A61B 5/11* (2006.01)
*A61B 90/00* (2016.01)

(52) U.S. Cl.
CPC .............. *A61B 5/4566* (2013.01); *A61B 5/11* (2013.01); *A61B 5/6814* (2013.01); (Continued)

(58) Field of Classification Search
CPC ........ A61B 5/4566; A61B 5/11; A61B 5/6814
See application file for complete search history.

(56) References Cited

U.S. PATENT DOCUMENTS 1,398,871 A 11/1921 Livingston
1,487,998 A 3/1924 Woolf
(Continued)

FOREIGN PATENT DOCUMENTS

EP 3015056 A1 5/2016

OTHER PUBLICATIONS

Written Opinion of the International Searching Authority dated Sep. 8, 2021.
Beck, Center Punch, U.S. Pat. No. 5,7819,6A issued Mar. 2, 1897.

*Primary Examiner* — Daniel L Cerioni
(74) *Attorney, Agent, or Firm* — Jacob M. Ward; Ward Law Office LLC

(57) ABSTRACT

A cervical spine movement measuring device having a main frame having a plurality of arms for maintaining the head of a person in position and a torsion system adjustably attached to the main frame for positioning the torsion system, with an input shaft, relative to the main frame. The measuring device includes a main frame with a plurality of arms. The plurality of arms include at least one pad configured to hold the head. The input shaft connects to an isokinetic dynamometer via an interphase connector. An isokinetic dynamometer is configured to measure range of motion and torque of the wearer during an assessment. The device includes an input shaft positionable about pivot points. The input shaft is adjustably secured to the main frame. The measuring device allows for assessment and evaluation of cervical spine flexion, extension, right lateral flexion, left lateral flexion, right rotation, and left rotation.

8 Claims, 11 Drawing Sheets

(52) U.S. Cl.
CPC ............ *A61B 5/6831* (2013.01); *A61B 90/06* (2016.02); *A61B 2090/066* (2016.02)

(56) References Cited

U.S. PATENT DOCUMENTS

| | | | | |
|---|---|---|---|---|
| 2,727,510 | A | 12/1955 | Thompson | |
| 2,791,999 | A | 5/1957 | Bustamante | |
| 2,855,202 | A | 10/1958 | Kinne | |
| 2,882,892 | A | 4/1959 | Kosior | |
| 3,709,216 | A | 1/1973 | Hilyard et al. | |
| 4,066,259 | A | 1/1978 | Brentham | |
| 4,189,141 | A | 2/1980 | Rooney | |
| 4,219,193 | A | 8/1980 | Newman | |
| 4,278,249 | A | 7/1981 | Forrest | |
| 4,339,124 | A | 7/1982 | Vogler | |
| 4,357,011 | A | 11/1982 | Voris | |
| 4,528,990 | A | 7/1985 | Knowles | |
| 4,586,515 | A * | 5/1986 | Berger | A61B 5/1126 600/595 |
| 4,655,450 | A | 4/1987 | Rogers, Jr. et al. | |
| 4,832,333 | A | 5/1989 | Lockett | |
| 4,893,808 | A | 1/1990 | McIntyre et al. | |
| 4,902,009 | A | 2/1990 | Jones | |
| 4,989,859 | A | 2/1991 | Jones | |
| 5,324,247 | A | 6/1994 | Lepley | |
| 5,336,138 | A * | 8/1994 | Arjawat | A63B 23/025 482/136 |
| 5,997,440 | A | 12/1999 | Hanoun | |
| 6,473,717 | B1 | 10/2002 | Clausssen et al. | |
| 6,551,214 | B1 | 4/2003 | Taimela | |
| 7,556,607 | B2 | 7/2009 | Coates et al. | |
| 8,038,588 | B2 | 10/2011 | Hobson et al. | |
| 8,529,414 | B2 | 9/2013 | Hobson et al. | |
| 10,004,626 | B1 | 6/2018 | Stine | |
| 2004/0220500 | A1 | 11/2004 | Dahl | |
| 2007/0272010 | A1 | 11/2007 | O'Leary et al. | |
| 2009/0138040 | A1 | 5/2009 | Fallah | |
| 2010/0240504 | A1 | 9/2010 | Hobson et al. | |
| 2011/0111925 | A1 | 5/2011 | Hobson et al. | |
| 2020/0069998 | A1 | 3/2020 | Smith et al. | |

* cited by examiner

HEAD AND NECK FULL MOTION TESTING SYSTEM

CROSS REFERENCE TO RELATED APPLICATIONS

This application is a United States National Stage Application PCT/US2021/033115, filed on May 19, 2021, which in turn claims the benefit of U.S. Provisional Application Ser. No. 63/027,458, filed on May 20, 2020. The entire disclosures of the above applications are incorporated herein by reference.

FIELD

The present invention relates generally to range of motion assessment devices and, more particularly, to cervical spine assessment devices.

INTRODUCTION

This section provides background information related to the present disclosure which is not necessarily prior art.

Neck pain affects much of the population and many people will experience neck pain at some point in their life. Traumatic neck injury, such as whiplash, is a commonly reported injury in some areas. In recent years, substantial evidence has emerged identifying various impairments in the neck muscle system, which are invariably accompanied by chronic neck pain.

Additionally, a lack of strength in the muscles of the neck can render an individual, especially an athlete, more susceptible to injury. While this is well documented, there are a dearth of devices to easily measure and assess both strength and range of motion in the most relevant axes. Further, it has generally been recognized that the neck musculature of an athlete can be developed through exercise so as to reduce the chance of injury. Additionally, neck exercises may be prescribed for rehabilitation following injury. In either case, it is considered important to assess all of the neck musculature, including not only those muscles which provide for flexion and extension of the head forward, backward, and laterally, but also those muscles which provide for rotational movement of the head. An example of a device for measuring rotational movement of the head is disclosed in U.S. Pat. No. 4,655,450 to Burton Rogers, the entire disclosure of which is incorporated herein by reference.

Known exercising devices lack an ability to provide meaningful tracking and databasing of a patient's strength, endurance, power, and torque output at each point in assessing a range of motion. More particularly, the known measuring devices are not configured to provide a practitioner with real time analysis of the patient's improvement over time using existing machines and data. For example, the Multi-Cervical Unit, made by BTE Technologies (Hanover, MD), incorporates a computer system that records and interprets a patient's range of motion and strength. However, the device does not provide generalized feedback in terms known to those of skill in the art, and instead uses a proprietary software to create a strengthening regime that can only be accomplished using the same device. Thus, there is no device available that can assess an individual's cervical spine range of motion and strength using readily transportable equipment and quantification. Without using a standardized machine and/or criteria, there can be issues with repeatability and measurement accuracy.

There is a continuing need for a measuring and assessing device that provides the ability to measure various patient outputs in all ranges of motion.

SUMMARY

In concordance with the instant disclosure, a cervical spine movement measuring device that provides the ability to measure various patient outputs in all directions during an exercise, has been surprisingly discovered.

In one embodiment, the measuring device may have a main frame. The main frame may have a plurality of arms. Each of the arms may have at least one pad. The at least one pad is configured to hold a head of a patient. A torsion system is adjustably attached to the main frame for positioning the main frame and connecting with an isokinetic dynamometer. The measuring device has an input shaft that is positionable about a plurality of pivot points. The input shaft is adjustably secured to the main frame.

Further areas of applicability will become apparent from the description provided herein. It should be understood that the description and specific examples are intended for purposes of illustration only and are not intended to limit the scope of the present disclosure.

DRAWINGS

The above, as well as other advantages of the present disclosure, will become readily apparent to those skilled in the art from the following detailed description, particularly when considered in the light of the drawings described hereafter.

FIG. 1 is a perspective view of the measuring device according to an embodiment of the present disclosure;

FIGS. 2A-2H are schematic views depicting ranges of motion for assessment, FIGS. 2A and 2B show flexion which is measured from 0-90 degrees from a neutral position with FIG. 2A showing the neutral position, FIGS. 2C and 2D show extension which is measured from 0-90 degrees from a neutral position with FIG. 2C showing the neutral position, FIGS. 2E and 2F show lateral flexion which is measured from 0-90 degrees from a neutral position with FIG. 2E showing the neutral position, and FIGS. 2G and 2H show rotation which is measured from 0-90 degrees from the neutral position with FIG. 2G showing the neutral position;

FIGS. 3A-3E show an embodiment of a method for using the measuring device in accordance with the present disclosure, wherein FIG. 3A shows the head positioning device positioned on a person's head, FIG. 3B shows the main frame being positioned about the person's head, FIG. 3C shows the positioning of the measuring device for use in assessing lateral flexion, FIG. 3D shows the positioning of the measuring device for use in assessing flexion and extension, and FIG. 3E shows the positioning of the measuring device for use in assessing rotation;

FIGS. 4A and 4B show the position of the person being assessed when using the measuring device of the present disclosure, wherein FIG. 4A shows the person in a prone position and FIG. 4B shows the person seated and side lying;

Figure 10A:
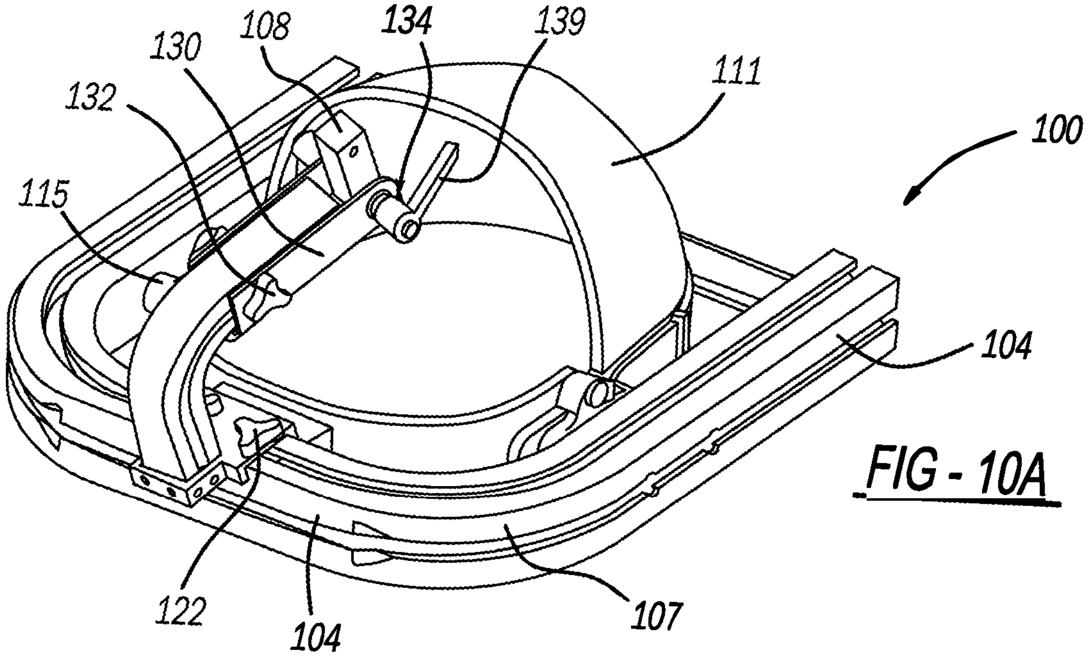
Figure 10B:
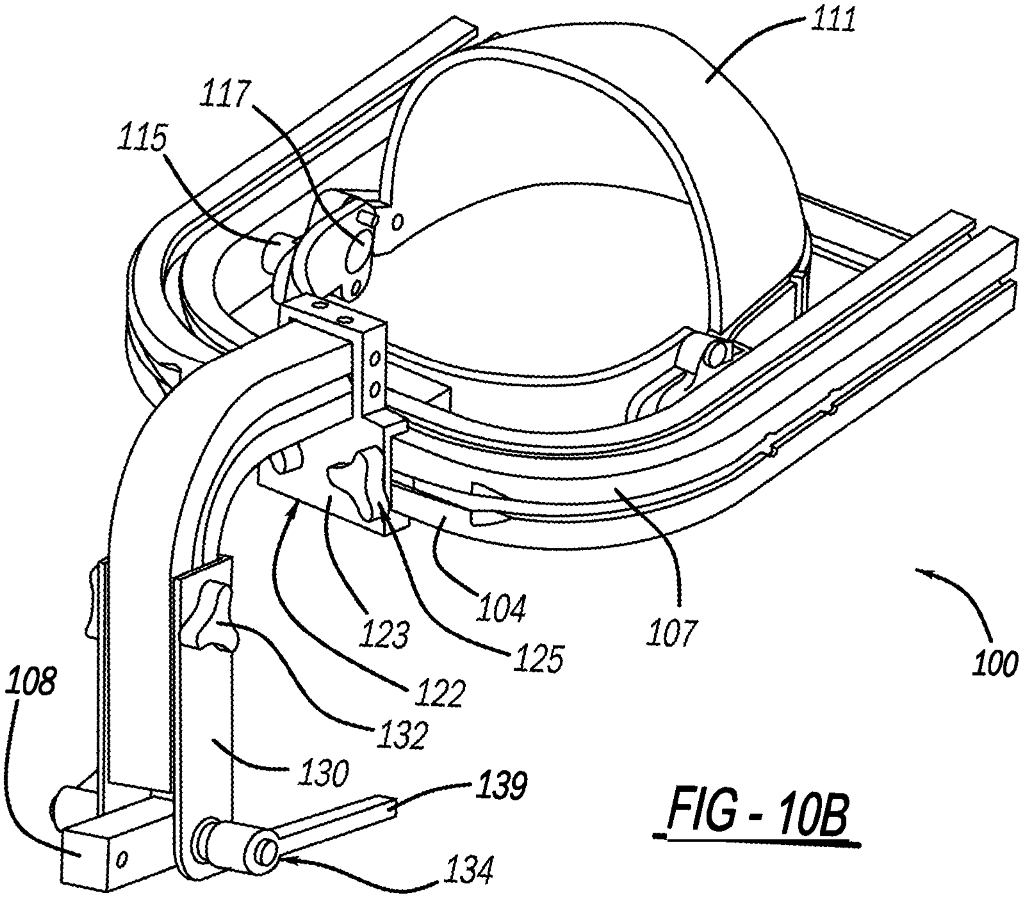
Figure 10C:
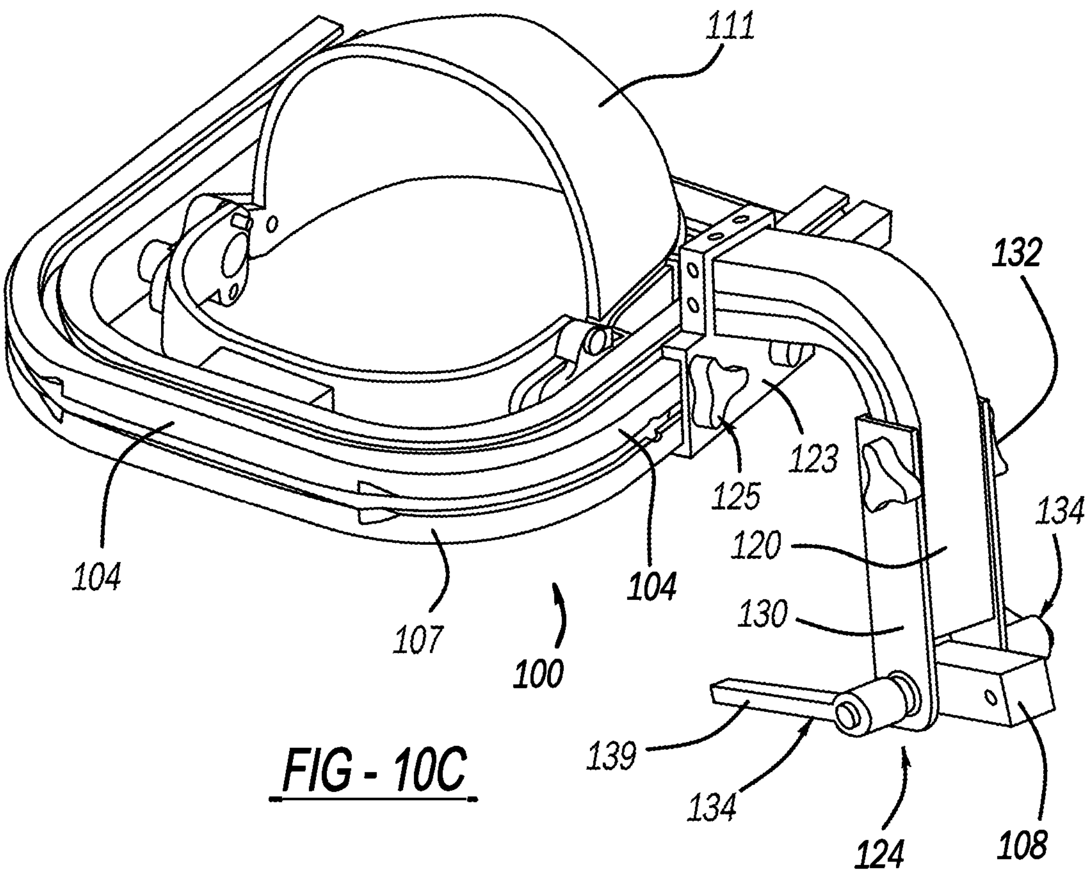
Figure 11A:
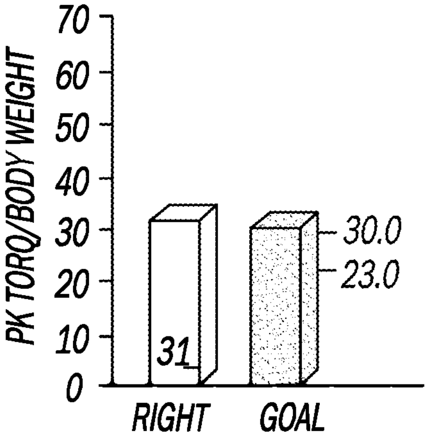
Figure 11B:
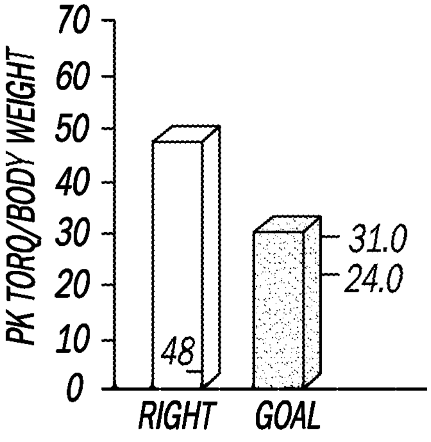
Figure 11C:
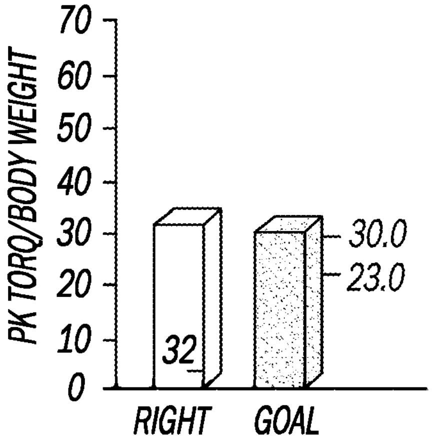
Figure 11D:
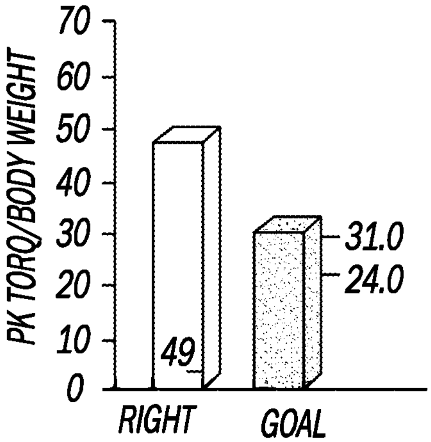

FIGS. 10A-10C are perspective views showing the positioning of the measuring device relative to the head positioning device during an assessment, with FIG. 10A showing positioning during rotational motion assessment, FIG. 10B showing positioning during lateral flexion motion assessment, and FIG. 10C showing positioning during flexion and extension motion assessment; and FIGS. 11A-11D are examples of a graphical data output provided by the measuring device via an isokinetic dynamometer according to an embodiment of the present disclosure.

DETAILED DESCRIPTION

The following description of technology is merely exemplary in nature of the subject matter, manufacture and use of one or more inventions, and is not intended to limit the scope, application, or uses of any specific invention claimed in this application or in such other applications as may be filed claiming priority to this application, or patents issuing therefrom. Regarding methods disclosed, the order of the steps presented is exemplary in nature, and thus, the order of the steps can be different in various embodiments, including where certain steps can be simultaneously performed, unless expressly stated otherwise. "A" and "an" as used herein indicate "at least one" of the item is present; a plurality of such items may be present, when possible. Except where otherwise expressly indicated, all numerical quantities in this description are to be understood as modified by the word "about" and all geometric and spatial descriptors are to be understood as modified by the word "substantially" in describing the broadest scope of the technology. "About" when applied to numerical values indicates that the calculation or the measurement allows some slight imprecision in the value (with some approach to exactness in the value; approximately or reasonably close to the value; nearly). If, for some reason, the imprecision provided by "about" and/or "substantially" is not otherwise understood in the art with this ordinary meaning, then "about" and/or "substantially" as used herein indicates at least variations that may arise from ordinary methods of measuring or using such parameters.

All documents, including patents, patent applications, and scientific literature cited in this detailed description are incorporated herein by reference, unless otherwise expressly indicated. Where any conflict or ambiguity may exist between a document incorporated by reference and this detailed description, the present detailed description controls.

When an element or layer is referred to as being "on," "engaged to," "connected to," or "coupled to" another element or layer, it may be directly on, engaged, connected or coupled to the other element or layer, or intervening elements or layers may be present. In contrast, when an element is referred to as being "directly on," "directly engaged to," "directly connected to" or "directly coupled to" another element or layer, there may be no intervening elements or layers present. Other words used to describe the relationship between elements should be interpreted in a like fashion (e.g., "between" versus "directly between," "adjacent" versus "directly adjacent," etc.). As used herein, the term "and/or" includes any and all combinations of one or more of the associated listed items.

Spatially relative terms, such as "inner," "outer," "beneath," "below," "lower," "above," "upper," and the like, may be used herein for ease of description to describe one element or feature's relationship to another element(s) or feature(s) as illustrated in the figures. Spatially relative terms may be intended to encompass different orientations of the device in use or operation in addition to the orientation depicted in the figures. For example, if the device in the figures is turned over, elements described as "below", or "beneath" other elements or features would then be oriented "above" the other elements or features. Thus, the example term "below" can encompass both an orientation of above and below. The device may be otherwise oriented (rotated 90 degrees or at other orientations) and the spatially relative descriptors used herein interpreted accordingly.

The cervical spine movement measuring device of the present disclosure allows any facility with a dynamometer (e.g., an anisometric dynamometer) to assess and quantitate both the range of motion and the strength of the cervical spine of an individual. This is an important advancement because recent studies have indicated that the strength of the cervical spine is more vitally important than was once understood. Additionally, the ability to configure the device to be used with existing dynamometers allows performing assessments that are understood industry-wide, without requiring additional machinery or specialized training. The universal nature of the device has long been needed and the ability to use more easily recognized quantifiable numbers is shown by the lack of adoption of the existing devices. Had the currently available devices provided the necessary framework, then there would have been wider adoption and use thereof. Instead, the industry remains in need of the functionalities provided by the present device.

With reference to FIGS. 1-11, a cervical spine movement measuring device, generally shown at 100, can be configured to hold a head of a patient during a predetermined assessment and evaluation session. The measuring device 100 can be designed to interface with a dynamometer, which can include an isokinetic dynamometer 101 as depicted in the figures. The isokinetic dynamometer 101 can be configured to perform measurements relative to a movement of the head and cervical spine of the patient. These measurements are discussed in greater detail herein below.

In general, the isokinetic dynamometer 101 can include a device accommodating resistance for applied forces and controls a speed of exercise at a predetermined rate. Any isokinetic dynamometer can be used in connection with the present disclosure, examples of which are well known to those of skill in the art. An example of an acceptable isokinetic dynamometer is the SYSTEM 4 PRO™, which is commercially available from BIODEX, located in Shirley, New York. A skilled artisan may select other suitable commercially available isokinetic dynamometers 101, as desired, without departing from the spirit of the present disclosure.

It should be appreciated that the measuring device 100 can be configured to evaluate and assess an entirety of a cervical spine musculature of the patient. More particularly, the measuring device 100 can allow for evaluation and assessment of various types of cervical spine movement, including one or more of flexion, extension, right lateral flexion, left lateral flexion, right rotation, and left rotation. The measuring device 100 can provide a quantifiable, objective assessment of the musculature to the operator or user of the measuring device 100 (not the patient or person being assessed). The objective assessment can be further used as a baseline measurement against which additional measurements are compared. Alternatively, or additionally, the objective assessment can provide diagnosis of an underlying health concern or susceptibility.

Figure 2A:
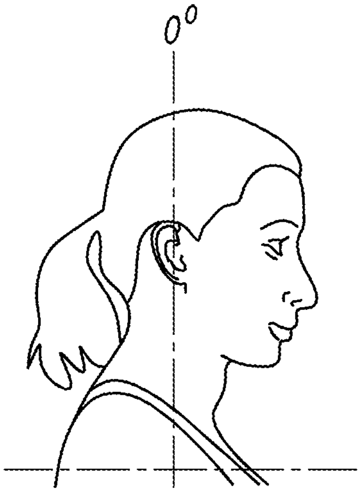
Figure 2B:
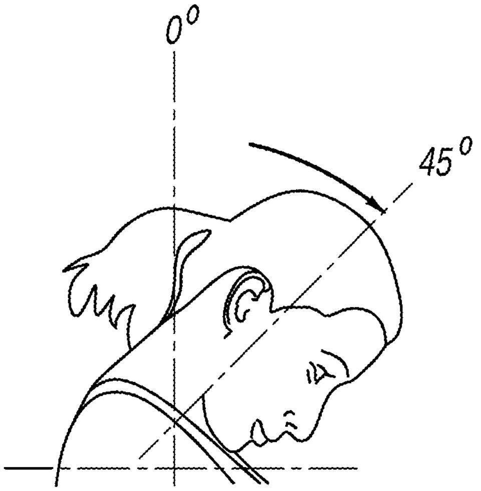
Figure 2C:
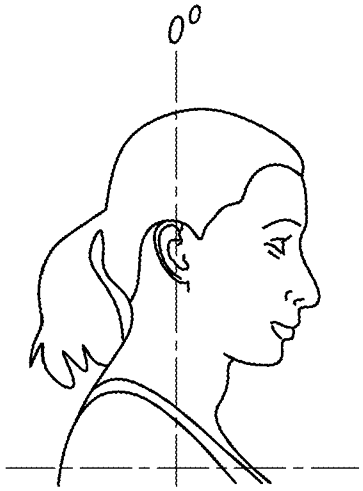
Figure 2D:
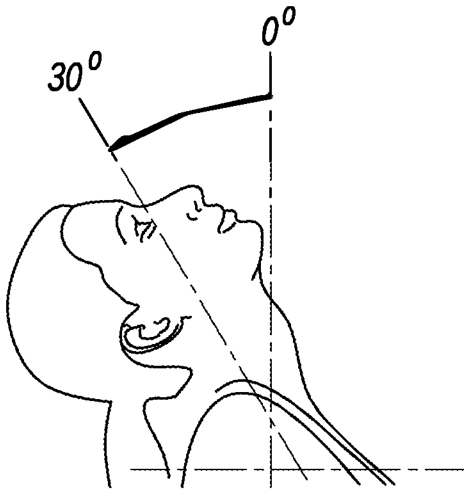
Figure 2E:
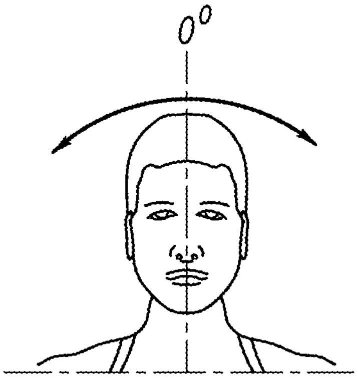
Figure 2F:
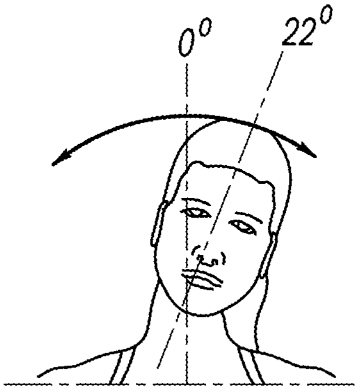
Figure 2G:
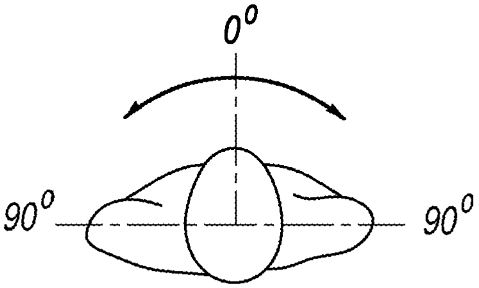
Figure 2H:
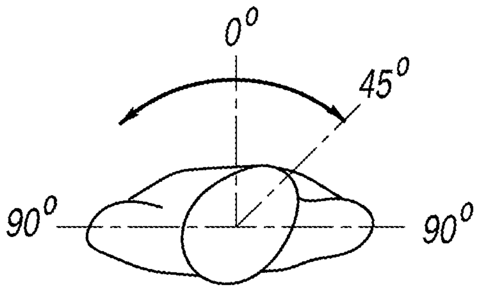
Figure 3A:
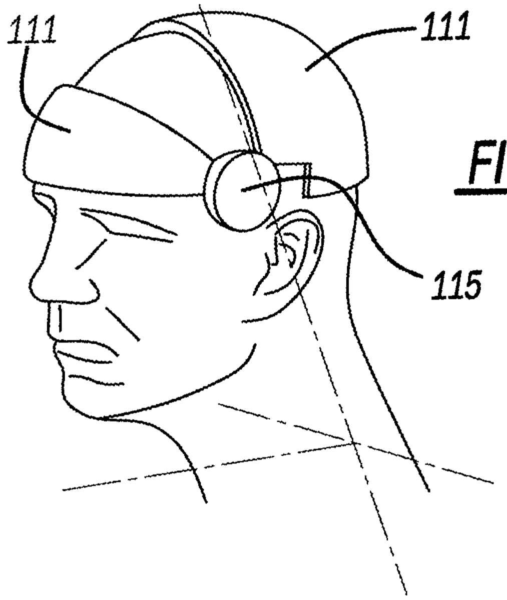
Figure 3B:
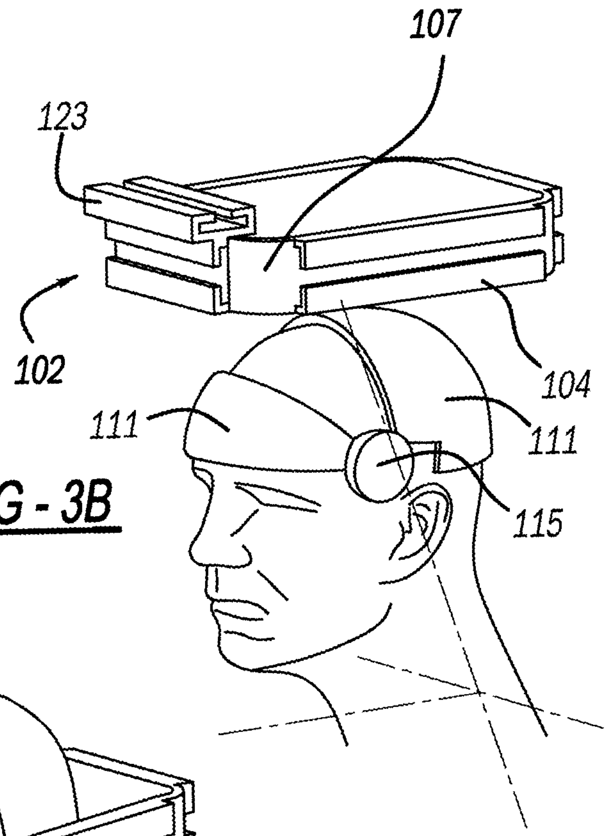
Figure 3C:
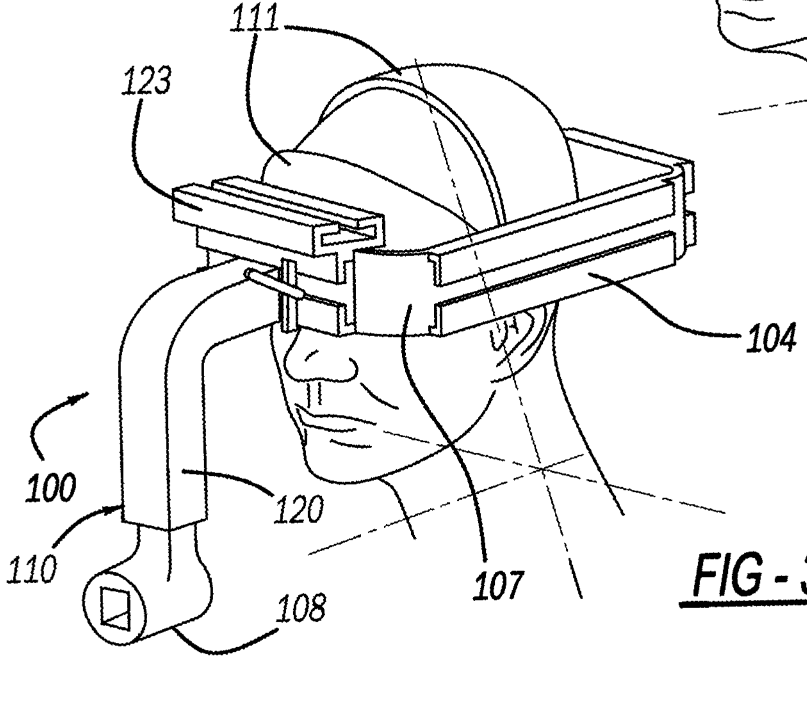
Figure 3D:
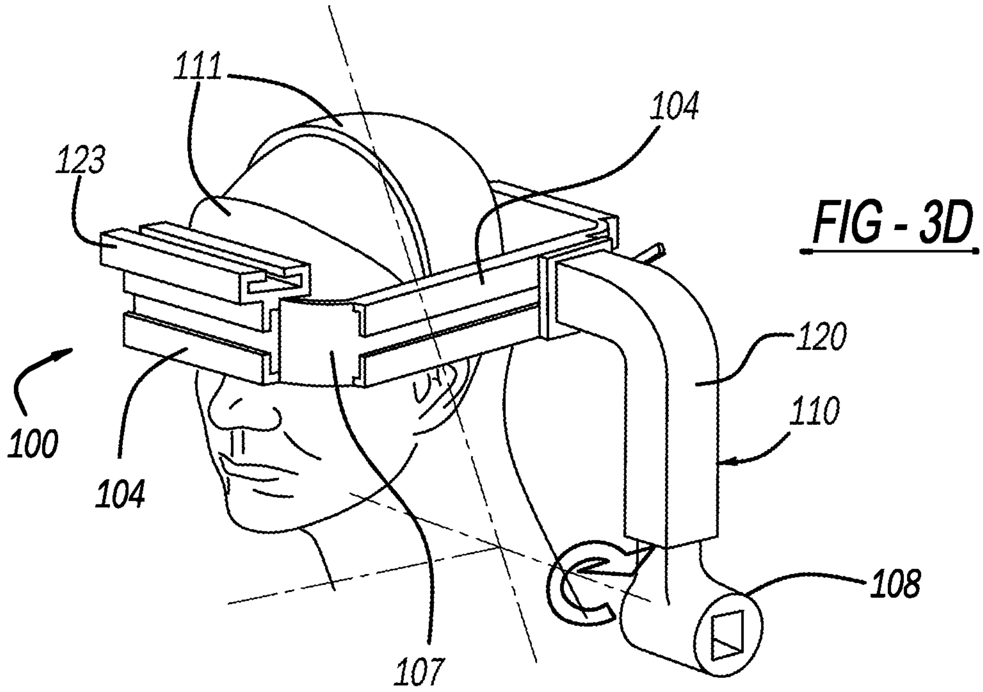
Figure 3E:
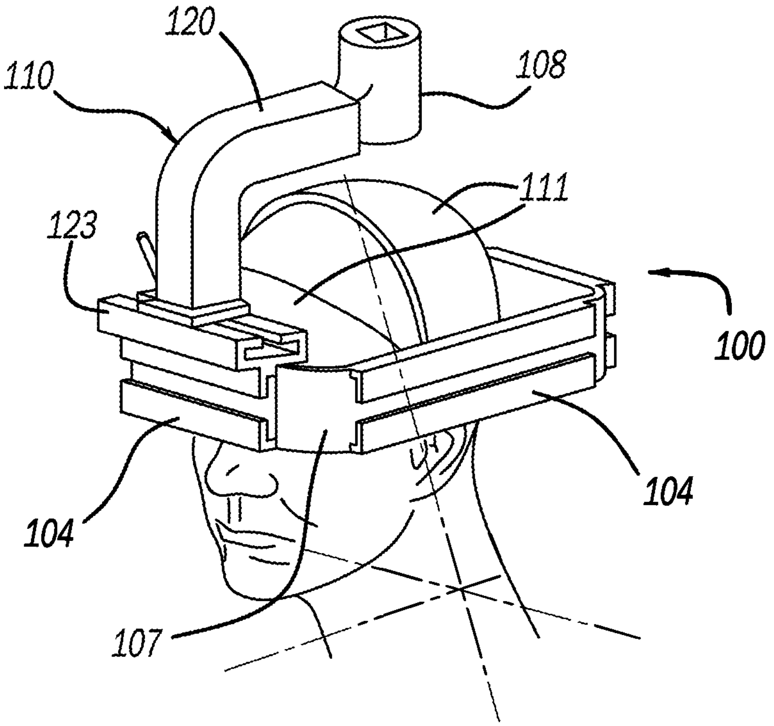
Figure 4A:
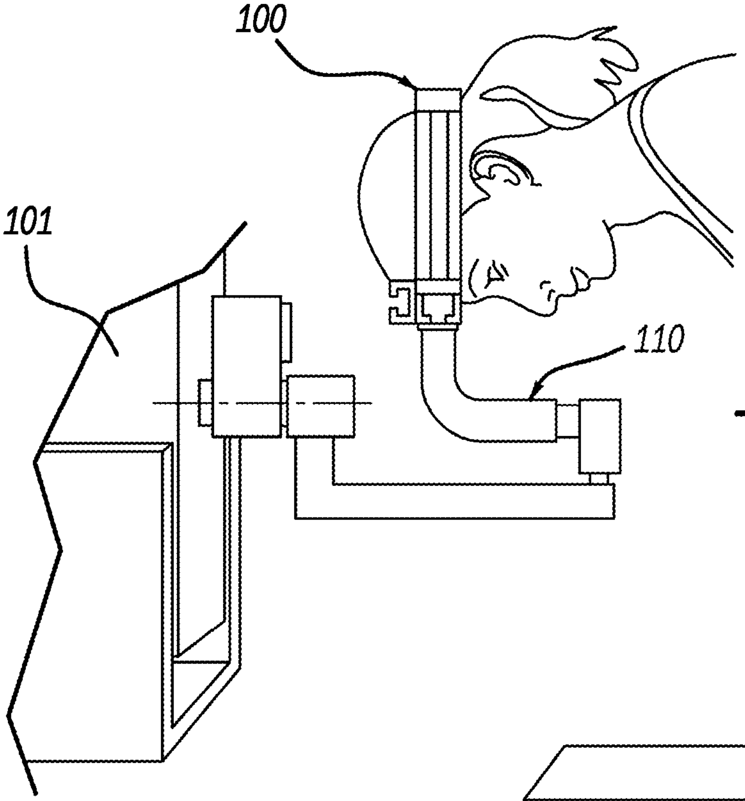
Figure 4B:
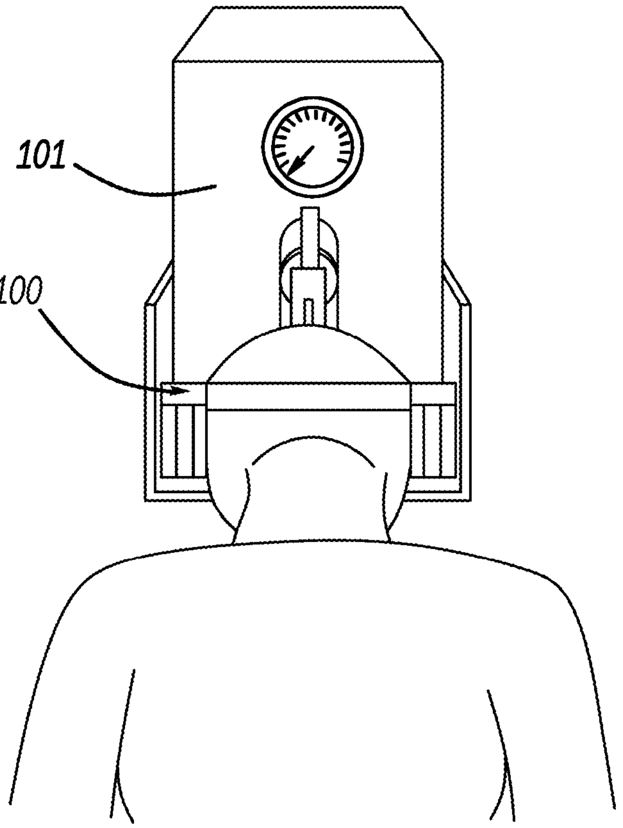

FIGS. 2A-H provide depictions of the certain ranges of motion that can be assessed using the measuring device 100. As shown in FIGS. 2A and 2B, flexion may be defined as a movement in which a chin of a patient is lowered to a chest of the patient. Extension is defined a movement in which the chin of the patient is raised such that the patient's eyes are pointed upward (see FIGS. 2C and 2D). Right lateral flexion and left lateral flexion are defined as a movement in which an ear of a patient is moved toward the respective shoulder on a same side of the patient (see FIGS. 2E and 2F). Right lateral rotation and left lateral rotation are defined as a movement in which the head is rotated in the respective direction (see FIGS. 2G and 2H).

The measuring device 100 of the present disclosure can allow for a use of one device to measure and assess anywhere from a single region to multiple regions, to an entirety of the cervical spine musculature. Advantageously, the measuring device 100 can be used in conjunction with well-known isokinetic dynamometers 101, so additional training is not required nor is additional large equipment required. Also, the use of well-known equipment enables the user to better understand and utilize the assessment results. Further, the use of a single device can minimize an amount of cleaning and sanitizing required between patients.

The measuring device 100 can include a main frame 102. The main frame 102 can be generally rectangular in shape. The main frame 102 can also be configured to connect to the isokinetic dynamometer 101. The main frame 102 can be fabricated from a resilient material capable of transferring the load from the head positioning device 111 to the isokinetic dynamometer 101. Non-limiting examples of such materials include, but are not limited to, lightweight metals, such as aluminum, and thermoplastic materials. As non-limiting examples, the thermoplastic material may be one of polycarbonate, polypropylene, and polyethylene. Advantageously, the thermoplastic material provides sufficient durability, while also being lightweight, which allows for easy transport. A skilled artisan may select other suitable materials that are lightweight and durable for use as the main frame 102.

The main frame 102 can include a plurality of arms 104. The plurality of arms 104 can be formed of a resilient material and can include various structures, where a non-limiting example includes an extruded aluminum T-slot rail. For example, T-slot rail can include lengths of square or rectangular extruded aluminum (e.g., 6105-T5 aluminum alloy) with a T-slot down the centerline of one or more sides. T-slot rail includes structures also referred to as 80/20 rail or framing, after designs provided by 80/20, Inc. (Columbia City, IN).

The T-slot rails can be approximately 15-30 cm long and preferably 25 cm long and can be joined at either end 105. Each of the arms 104 can be coupled to one another at the ends 105 of each arm 104. The arms 104 can be coupled either directly between two adjacent ends 105 or via a connector 107. The connector 107 can be preferably formed of the same material as the arms 104 the main frame 102. The plurality of arms 104 can be configured to secure the head of the wearer in a specific orientation, when assessing the wearer using the measuring device 100. More specifically, the plurality of arms 104 can include three or four arms. As shown in the FIGS. 1, 3, and 5-10, the plurality of arms 104 can completely surround the head of the patient or can form a U-shape.

On one or more inside surfaces 109 of the plurality of arms 104, one or more pads 106 can be affixed to contact the head of the patient being assessed. The pad(s) 106 can be located at a generally central position on each of the arms 104. The pads 106 can be configured to contact and stabilize the head of the patient. The pads 106 can also be used for attachment of the head positioning device 111. For example, the pads 106 can include attachment devices 113 that engage mating attachment devices 115 on the head positioning device 111 for removably attaching the head positioning device 111. Examples of such attachment devices 113, 115 include, but are not limited to, clips, hook and loop fasteners, buttons, snaps, an aperture combined with an attachment piece. The pads 106 can be configured to maintain an orientation of the head of the patient throughout a particular movement of the assessment. Each of the pads 106 can be adjustable in order to form a proper fit with the head of the patient. The measuring device 100 can also include an optional security strap (not shown), which can be configured to secure the main frame 102 to the head of the patient.

Each of the pads 106 can include a relatively hard and inflexible block of material, such as wood, as a non-limiting example. The inflexible material may be surrounded by a layer of padding material, such as foam, as a non-limiting example. It should be appreciated that the padding material can be conforming, comfortable, and can return to an original or normal configuration to be able to conform to a contour of the next patient/athlete. The foam can be covered by a suitable enclosure material, such as vinyl plastic, as a non-limiting example. A skilled artisan can select other suitable materials to form the pads 106 within the scope of the present disclosure.

The head positioning device 111 can be fabricated from a thermoplastic material. As non-limiting examples, the thermoplastic material can be one of polycarbonate, polyethylene terephthalate glycol, polypropylene, and polyethylene. Advantageously, the thermoplastic material provides sufficient durability when used with a measuring device 100, while also being lightweight, which can allow for easy transport in a medical setting. A skilled artisan can select other suitable materials that are lightweight, durable, and easy to clean and/or disinfect for use as the head positioning device 111. The head positioning device 111 can also include a liner made of a different material designed for comfort of the wearer. Additionally, the head positioning device 111 can include additional cushioning materials.

Figure 1:
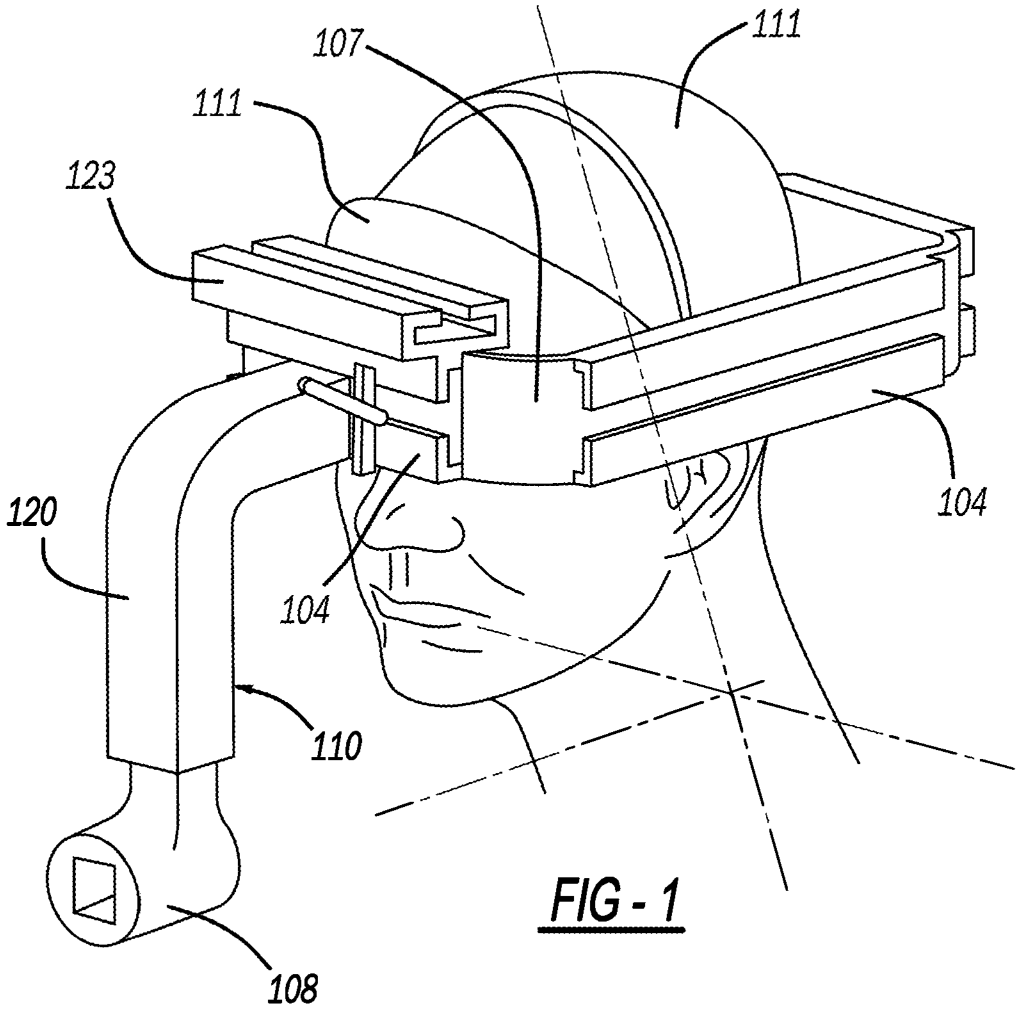
Figure 8A:
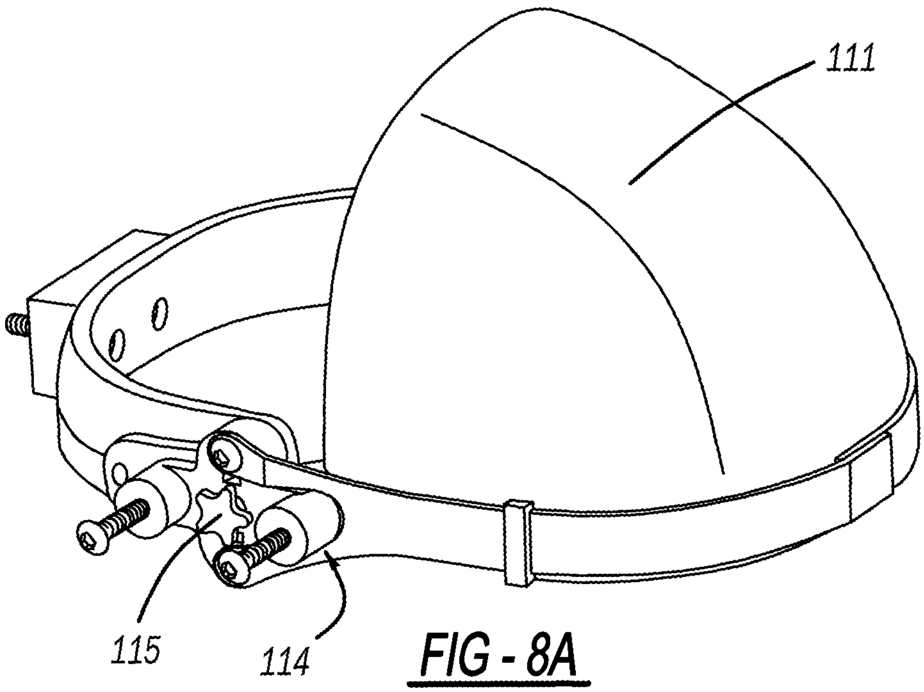
FIGS. 8A and 8B are perspective views of the head positioning device according to an embodiment of the present disclosure (FIG. 8A) and a close-up view of an adjustment device for adjusting the head positioning device (FIG. 8B)
Figure 8B:
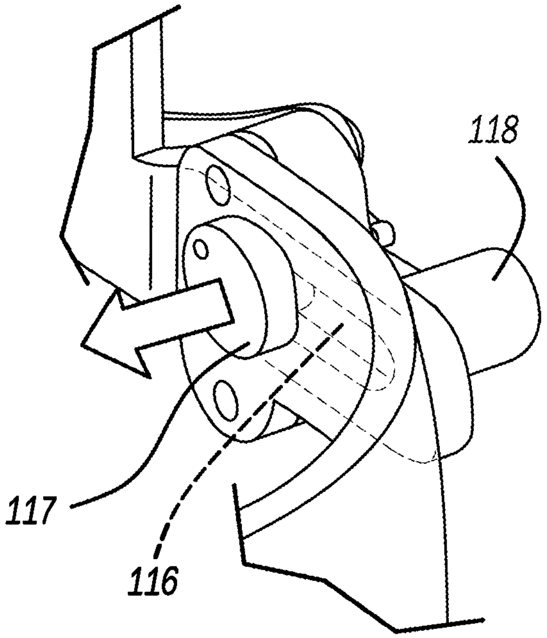
Figure 9:
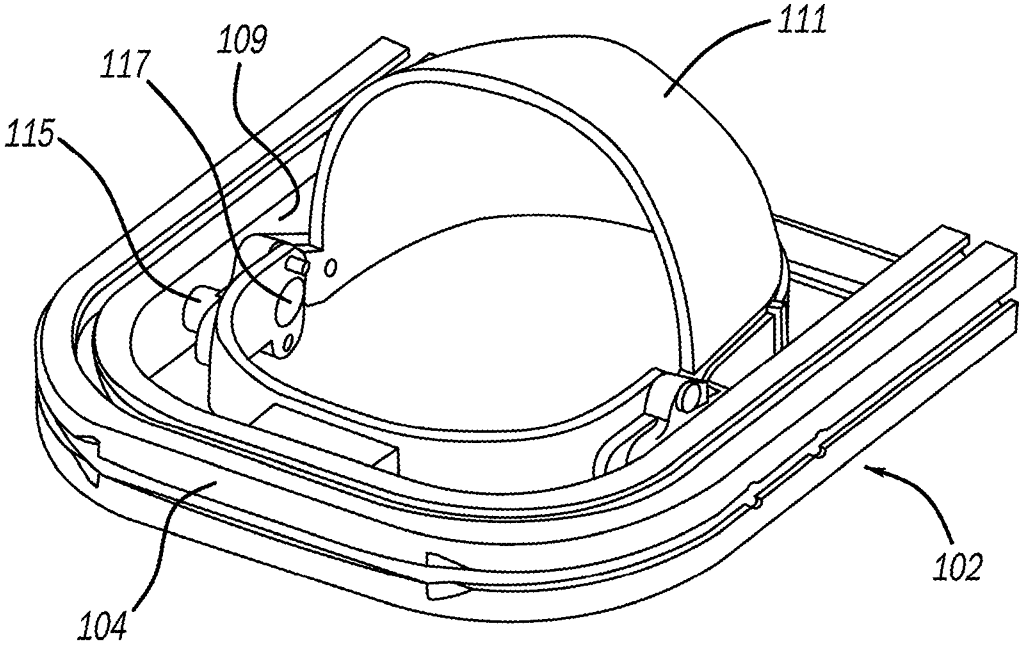
FIG. 9 is a perspective view of the head positioning device attached to the main frame of the measuring device according to an embodiment of the present disclosure.

The head positioning device 111 can be formed as a single piece, as shown in FIGS. 8-10 or as multiple pieces, as shown in FIGS. 1 and 3. If formed as a single piece, including a single unitary structure, the head positioning device 111 can include at least one adjustment device 114. The adjustment device 114, as shown in FIG. 8, can be located adjacent the attachment device 115, but it can be appreciated by a skilled artisan that the location of the adjustment device 114 can be moved without departing from the spirit of the present disclosure. More specifically, the adjustment device 114 can include a slot 116 in the head positioning device 111 and an adjustment block 118, wherein the adjustment block 118 can engage the slot 116 in a tight fit manner and includes at least one knob 117 for moving the adjustment block 118 within the slot 116 for adjusting the fit of the head positioning device 111.

Figure 5:
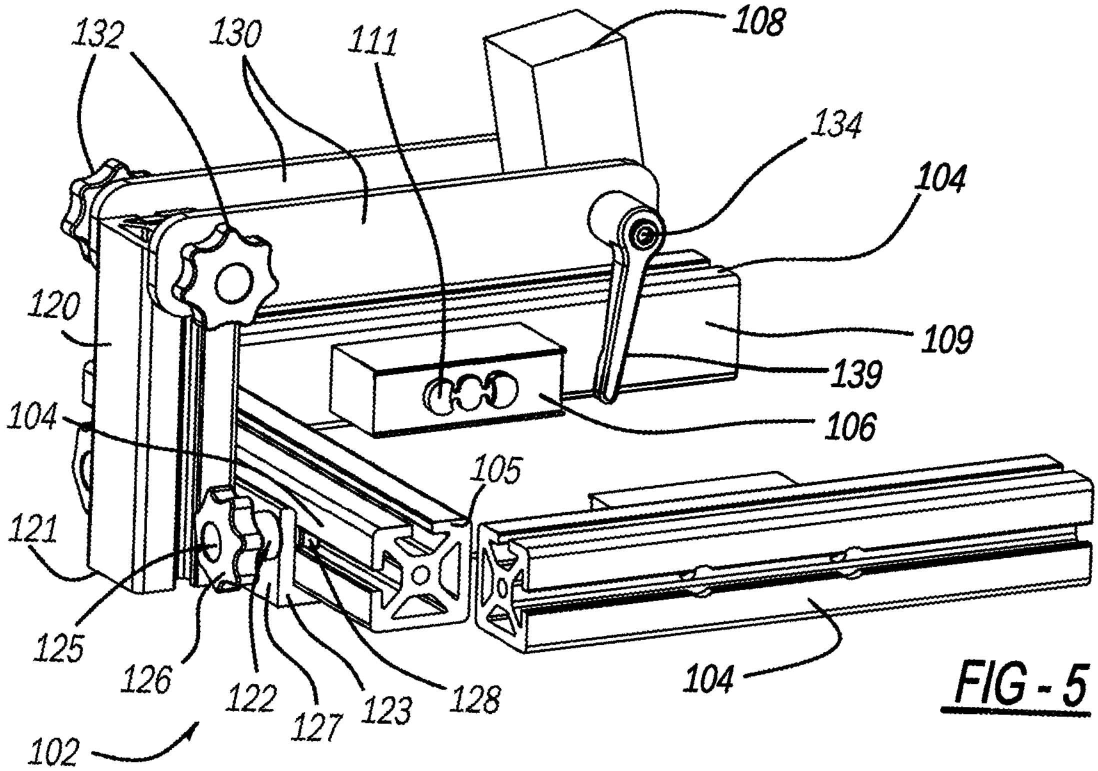
FIG. 5 is a partially exploded perspective view of the measuring device according to an embodiment of the present disclosure, depicting the measuring device during assessment of rotational motion.
Figure 6:
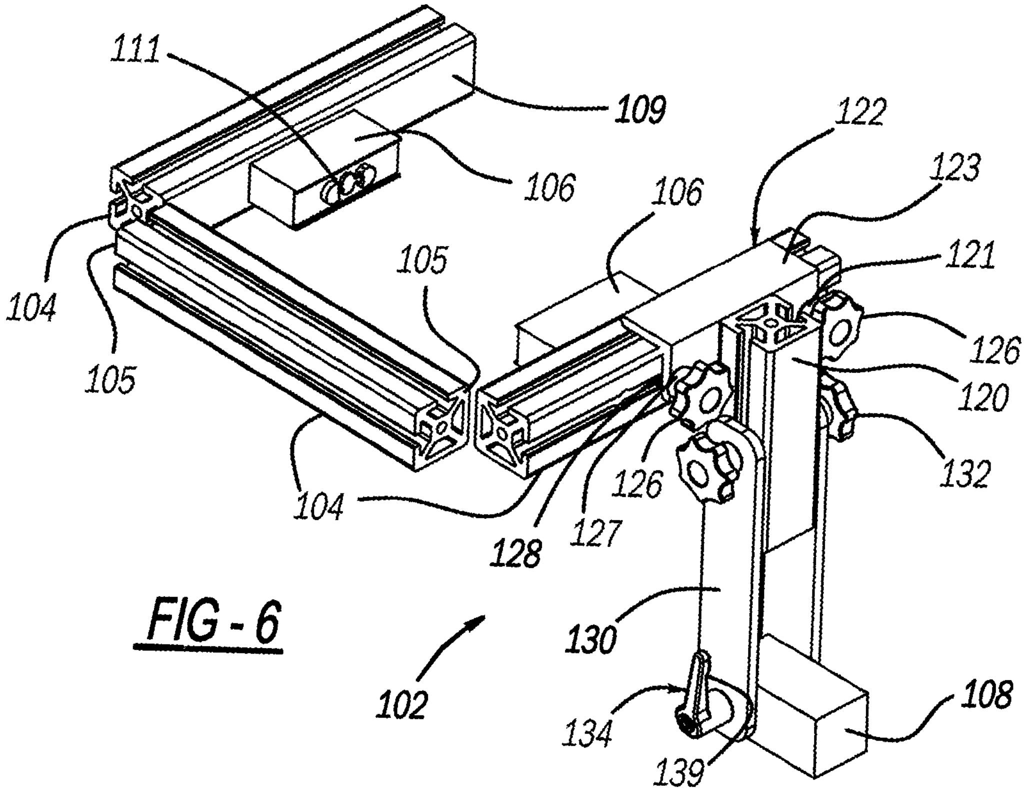
FIG. 6 is a partially exploded perspective view of the measuring device according to an embodiment of the present disclosure, depicting the measuring device during assessment of flexion and extension motion.
Figure 7:
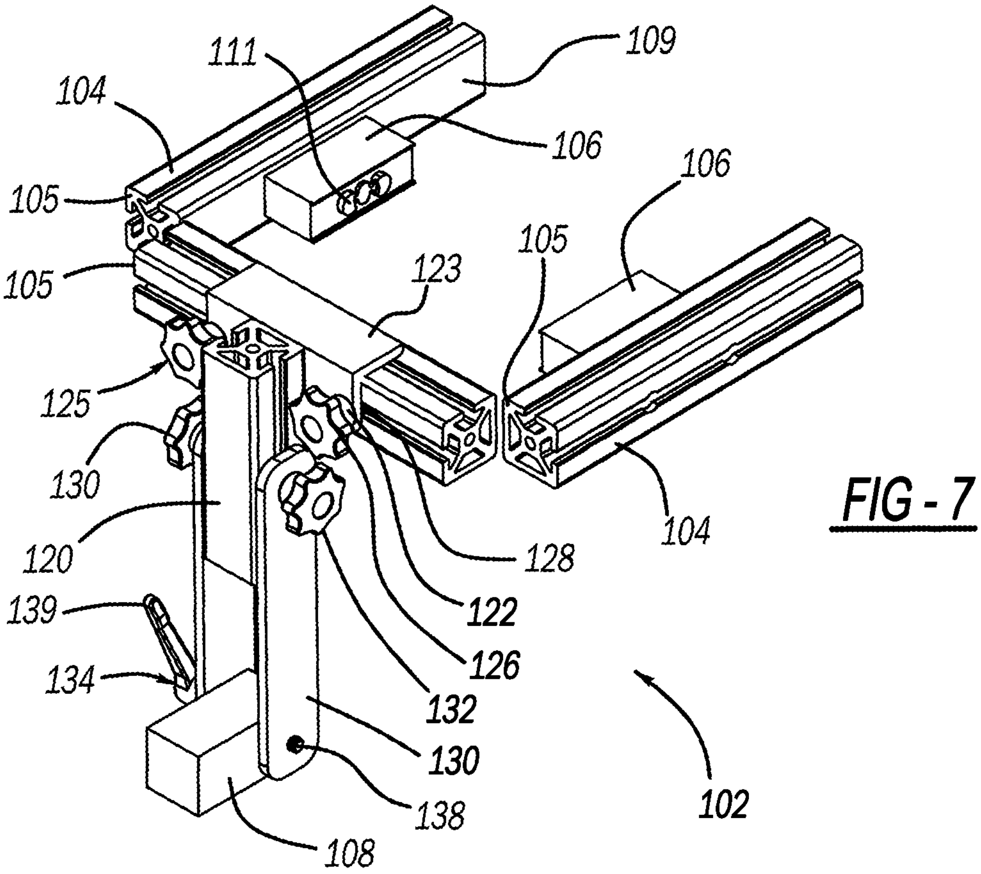
FIG. 7 is a partially exploded perspective view of the measuring device according to an embodiment of the present disclosure, depicting the measuring device during assessment of lateral flexion motion.

The isokinetic dynamometer 101 and the main frame 102 can be connected via a torsion system, which can include an input shaft 110. The input shaft 110 can be configurable about a plurality of pivot points, for example, as shown in FIGS. 5-7. The input shaft 110 can include a plurality of predetermined positions depending on the movement to be measured in the patient. The input shaft 110 can further define an axis of rotation for each of the measurements.

The input shaft 110 can include a main body 120, a main frame connector 122 and an orientation device 124. The main body 120 can be formed of the same material and configurations as the plurality of arms 104 of the main frame 102, where one non-limiting example is an aluminum T-slot rail. The main body 120 can be adjustably secured to the main frame 102 via a main frame connector 122. The main frame connector 122 can be rigidly affixed to the main body 120 at the connecting end 121 of the main body 120. The main frame connecter 122 can be adjustably secured to the main frame thereby allowing the input shaft 110 to be placed in different positions on the plurality of arms 104 of the main frame 102. The main frame connector 122 can include a main frame connection plate 123 and at least one adjustment knob 125. The connector plate 123 can be formed to engage at least 2 sides of the T-slot rails of the plurality of arms 104, to maintain the input shaft in the proper orientation. The connector plate 123 can further include at least one threaded aperture (not shown) for receiving the adjustment knob 125. Each adjustment knob 125 can include a handle 126 and a helical screw 128 for engaging the threaded aperture of the connector plate 123. Each adjustment knob 125 can also include a nut 127 for assisting in maintaining the connector plate 123 in position.

The main body 120 can be adjustably attached to an orientation device 124 at the end of the main body 120 opposite the connecting end 121. In certain embodiments, the orientation device 124 can include at least two plates 130, adjustment knobs 132, a pivoting device 134, and an interphase connector 108. The two plates 130 can be positioned about opposite side of the main body 120 and can be formed with a generally flat surface and an engagement pin (not shown) to engage the main body 120 on an interface side. For example, the engagement pin can be designed to rest within the slots of the T-slot rails that can be used as the main body 120 but can also allow the plates 130 to pivot the orientation of the main body 120 (See for example FIG. 5). The plates 130 can also include at least one threaded aperture (not shown). The threaded aperture can be designed to receive a threaded portion (not shown) of the adjustment knob 132. The plate can also include at least one additional aperture (not shown) for receiving the pivoting device 134. The pivoting device 134 can include a pin 138 and a handle 139. The pivoting device 134 can be used to position the interphase connector 108 relative to both the main frame 102 and the isokinetic dynamometer 101.

The interphase connector 108 can be in electronic communication with the isokinetic dynamometer 101. More particularly, the interphase connector 108 can allow for the evaluation of the cervical spine musculature of the patient by providing measurements based on the particular movement performed by the wearer. A specific orientation of the interphase connector 108 can be determined by specific cervical spine levels and corresponding anatomical landmarks.

The electronic communication can occur when the device, connected to the interphase connector 108 on the input shaft 110 generates torque through the input shaft 110 and the isokinetic dynamometer 101 generates one or more data sets.

The main frame 102 can include a plurality of attachment positions for the input shaft 110. In particular, each attachment position can place the main frame 102, and thus the head of the patient, into a predetermine orientation, relative to the cervical spine, for each movement to be measured. Advantageously, the main frame 102 can be utilized for all measurements in the exercise. Further, the plurality of attachment points can allow for consistent measurements to be performed across multiple exercise and evaluation sessions as the main frame 104 can be consistently oriented via the plurality of attachment points.

Where the cervical spine flexion and extension are being measured, as shown in FIGS. 3 and 6, the input shaft 110 can be attached to the main frame 102 via an adjustable attachment position on a side of the main frame. The input shaft 110 can be arranged such that a first pivot point can be disposed between approximately a third cervical segment and a fourth cervical segment of the patient. It should be appreciated that the patient may be lying, standing, or sitting where the cervical spine flexion and/or extension is/are being measured. It should be appreciated that in all positions the patient can be properly stabilized to isolate the cervical spine movement patterns.

With reference to FIGS. 3 and 7, where the right and left lateral flexion movements are being measured, the input shaft 110 can be attached to the main frame 102 via an adjustable attachment position on a front of the main frame 102 such that the input shaft 110 can be positioned below the main frame 102. The input shaft 110 can be arranged such that a first pivot point is disposed between approximately a third cervical segment and a fourth cervical segment of the patient. It should be appreciated that the patient can be lying, standing, or sitting where the right and/or left lateral flexion movements is/are being measured.

Where the right and left lateral rotation movements are being measured, for example as shown in FIGS. 3 and 5 the input shaft 110 can be attached to the main frame 102 via an adjustable attachment position at the front of the main frame 102 such that the input shaft 110 can be positioned above the main frame 102. The input shaft 110 can be arranged such that the axis of rotation can be parallel with the isokinetic dynamometer 101. It should be appreciated the patient can be lying on the patient's/wearer's stomach, side, or seated where the right and left lateral rotation movements are being measured.

As discussed hereinabove, the measuring device 100 can measure one or more certain variables during an assessment. In particular, the measuring device 100 can measure variables including strength, power, torque, range of motion, and total work in the wearer or patient wearing the measuring device 100 during the movement.

The measuring device 100 and the isokinetic dynamometer 101 can provide certain graphical outputs, such as those shown in FIG. 11. These graphical outputs can be formed and displayed in real time and an also be recorded and stored. Further, the measuring device 100 via the isokinetic dynamometer 101 can create a database of certain measurements. The database may provide the previous assessed graphical data as an overlay during a subsequent assessment. Advantageously, a physician or clinician can therefore analyze changes in certain measurements in real time as the patient is utilizing the measuring device 100.

Additionally, the measuring device 100 can measure torque as a percentage of body weight of the wearer. Advantageously, this provides a relative torque measurement for the patient relative to body size.

The measuring device 100 may measure total work under a torque curve. Advantageously, this allows for a calculation of the combination of torque and range of motion.

The data provided by the measuring device 100 and the isokinetic dynamometer 101 can reflect a coefficient of variance. The coefficient of variance allows the physician or clinician to determine the reliability of the testing. In other words, the clinician may determine if the patient provided consistent effort and technique throughout testing.

The measuring device 100 and the isokinetic dynamometer 101 can calculate a ratio between antagonistic and agonist muscle groups. This can allow for a calculation between the right and left side of the cervical spine. For example, the clinician can determine a difference in strength between the right lateral flexion and the left lateral flexion. Advantageously, the physician can use this difference to determine if the patient is at risk for an injury based on a muscle imbalance.

The measuring device 100 and the isokinetic dynamometer 101 can calculate acceleration time in milliseconds. The acceleration the time can include the time it takes to produce torque at a selected speed. The measuring device 100 and the isokinetic dynamometer 101 can also calculate deceleration time in milliseconds. The deceleration time can include the time it takes to go from a maximal speed to zero.

The graphical data provided by the measuring device 100 and the isokinetic dynamometer 101 can calculate torque decay, or a sudden dip in the torque curve. Torque decay can be reflective of a weaker or painful portion of the range of motion. Advantageously, the physician can highlight the weaker portions in real time.

In operation, the clinician can place the main frame 102 of the measuring device 100. The input shaft 110 can be positioned based on the movement to be measured. The input shaft 110 can be attached to the correct attachment point on the main frame 102 based on the measurement to be performed. The patient can then perform the desired movement pattern. The clinician can study the graphical output in real time. The clinician can also database the output data to be used during subsequent evaluations.

In operation, as shown in FIGS. 3A-E, the patient or wearer can first place the head positioning device on their head and secures it in place using the adjustment device. The main frame can be attached to the head positioning device. The individual in charge of the assessment or measurement, then can align the torsion system depending on which range of motion or strength is being tested. The measuring device can then be connected to an isokinetic dynamometer and the measuring can commence. When being used as an assessment tool, the desired assessments are made and the individual in charge of the assessment is then provided with an analysis regarding the assessment.

In another use of the device, after the assessment has been completed, the device can then be used as a trainer or teacher to assist the wearer in strengthening the muscles in need thereof or for increasing the wearer's range of motion. This can be accomplished by adding additional resistance by slowing the speed to the device.

In another use of the device, after the assessment has been completed, the individual in charge of the assessment can review the analysis and provide a diagnosis or susceptibility analysis. Thus, the device can be used as a diagnostic tool. In this use, the individual in charge can correlate the results of the analysis to either a known disease condition or a known susceptibility, many of which are known to those of skill in the art. After such a diagnosis, the device can be used as described above to train or strengthen the muscles in need thereof. Some non-limiting examples include but are not limited to, concussion, torticollis, cervical dysfunction, and whiplash. Additionally, if used as part of a concussion protocol, a baseline test can be run for each individual. Then should a potentially concussive incident occur, the baseline test can be compared with the new test. Also, the baseline test can be used to provide an early warning of concussion susceptibility.

The results of all of these uses can be compiled into a database. The database can be used to provide valuable insight into disease progression, or disease susceptibility.

While certain representative embodiments and details have been shown for purposes of illustrating the invention, it will be apparent to those skilled in the art that various changes may be made without departing from the scope of the disclosure, which is further described in the following appended claims.

What is claimed is:

1. A device for measuring cervical spine movement of a head of a person, comprising:

a main frame having a plurality of arms for maintaining the head of the person in a position, each arm of the plurality of arms is disposed within a common plane, and each arm of the plurality of arms further includes at least one pad configured to hold the head of the person within the device;

a torsion system comprising an input shaft configured to selectively couple between a first position and a second position on at least one arm of the plurality of arms, and each arm of the plurality of arms includes a T-slot configured to selectively receive the input shaft of the torsion system; and an isokinetic dynamometer coupled to the torsion system via the input shaft, the isokinetic dynamometer configured to measure motion and torque; and a head positioning device configured to be worn on the head of the person and removably attached to the main frame, the head positioning device including at least one adjustment device configured to secure the head positioning device to the head of the person, thereby maintaining alignment of the head within the device, and a plurality of mating attachment devices, the plurality of mating attachment devices coupling the head positioning device to the main frame.

2. The device according to claim 1, wherein the input shaft includes a main frame connector configured to engage the T-slot of one arm of the plurality of arms.

3. The device according to claim 2, wherein the at least one pad includes an attachment device configured to engage one mating attachment device of the plurality of mating attachment devices.

4. The device according to claim 1, wherein the at least one adjustment device is configured to adjust a fit of the head positioning device.

5. A device for diagnosing cervical spine dysfunction of a head of a person, comprising:

a main frame having a plurality of arms for maintaining the head of the person in a position, each arm of the plurality of arms is disposed within a common plane, and each arm of the plurality of arms further includes at least one pad configured to hold the head of the person within the device;

a torsion system comprising an input shaft configured to selectively couple between a first position and a second position on at least one arm of the plurality of arms, and each arm of the plurality of arms includes a T-slot configured to selectively receive the input shaft of the torsion system; and an isokinetic dynamometer coupled to the torsion system via the input shaft, the isokinetic dynamometer configured to measure motion and torque; and a head positioning device configured to be worn on the head of the person and removably attached to the main frame, the head positioning device including at least one adjustment device configured to secure the head positioning device to the head of the person, thereby maintaining alignment of the head within the device, and a plurality of mating attachment devices, the plurality of mating attachment devices coupling the head positioning device to the main frame.

6. The device according to claim 5, wherein the head positioning means includes at least two straps.

7. A method of measuring cervical spine movement of a head of a person, comprising:

placing the device according to claim 1 on the head of the person; and measuring the cervical spine movement of the head of the person.

8. The method according to claim 7, further comprising analyzing the measurements of the cervical spine movement of the head of the person to detect a cervical dysfunction.

* * * * *